(12) United States Patent
Morita et al.

(10) Patent No.: US 10,856,828 B2
(45) Date of Patent: Dec. 8, 2020

(54) SUPPORT INFORMATION-GENERATION APPARATUS, WARNING INFORMATION-NOTIFICATION APPARATUS, AND SUPPORT INFORMATION-GENERATION METHOD

(71) Applicant: Canon Medical Systems Corporation, Otawara-shi (JP)

(72) Inventors: Chihiro Morita, Nasushiobara (JP); Tatsuya Kimoto, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 66 days.

(21) Appl. No.: 16/376,306

(22) Filed: Apr. 5, 2019

(65) Prior Publication Data
US 2019/0307410 A1    Oct. 10, 2019

(30) Foreign Application Priority Data

Apr. 10, 2018   (JP) .................................. 2018-075421

(51) Int. Cl.
| | | |
|---|---|---|
| *G06K 9/00* | (2006.01) | |
| *A61B 6/00* | (2006.01) | |
| *G06F 9/54* | (2006.01) | |
| *A61B 17/88* | (2006.01) | |
| *G06T 7/00* | (2017.01) | |

(52) U.S. Cl.
CPC ............ *A61B 6/5205* (2013.01); *A61B 17/88* (2013.01); *G06F 9/542* (2013.01); *G06K 9/00523* (2013.01); *G06K 9/00536* (2013.01); *G06T 7/0012* (2013.01); *G06T 2207/30012* (2013.01)

(58) Field of Classification Search
CPC ............ G06K 9/00523; G06K 9/00536; G06T 2207/30012; G06T 7/0012; G06F 9/542; A61B 6/5205; A61B 17/88
See application file for complete search history.

(56) References Cited

U.S. PATENT DOCUMENTS

| | | | |
|---|---|---|---|
| 2001/0034527 A1 | 10/2001 | Scribner et al. | |
| 2017/0196508 A1* | 7/2017 | Hunter | ................... A61B 17/70 |
| 2018/0140260 A1* | 5/2018 | Taguchi | ............... G03B 42/026 |
| 2019/0350657 A1* | 11/2019 | Tolkowsky | ............ A61B 46/20 |

FOREIGN PATENT DOCUMENTS

JP       2008-093477       4/2008

\* cited by examiner

*Primary Examiner* — Ping Y Hsieh
(74) *Attorney, Agent, or Firm* — Oblon, McClelland, Maier & Neustadt, L.L.P.

(57) ABSTRACT

According to one embodiment, a support information-generation apparatus includes processing circuitry. The processing circuitry extracts a vertebral body region from a medical image and calculates a first volume of a vertebral body targeted for treatment by percutaneous vertebroplasty. The processing circuitry estimates a second volume of the targeted vertebral body related to an estimated shape. The processing circuitry calculates, based on a difference between the first volume and the second volume, a volume of an object to be inserted so as to deform the targeted vertebral body into the estimated shape.

13 Claims, 9 Drawing Sheets

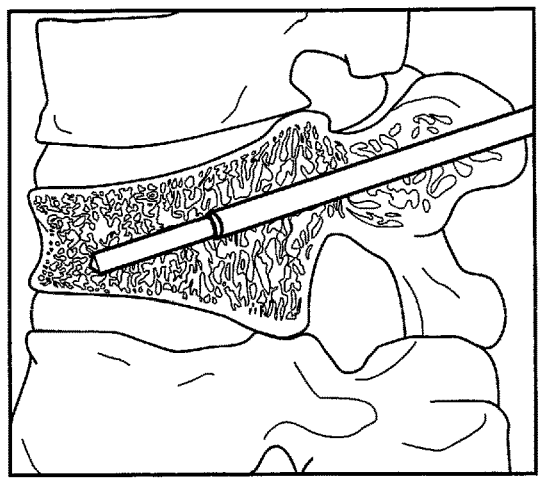
F I G. 5
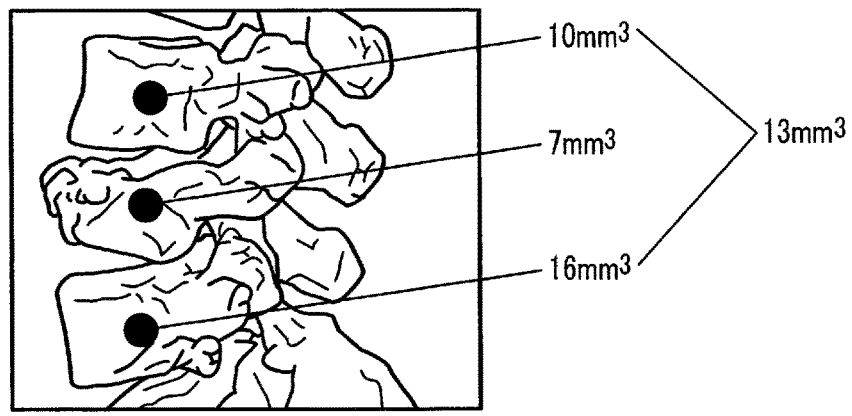
F I G. 6
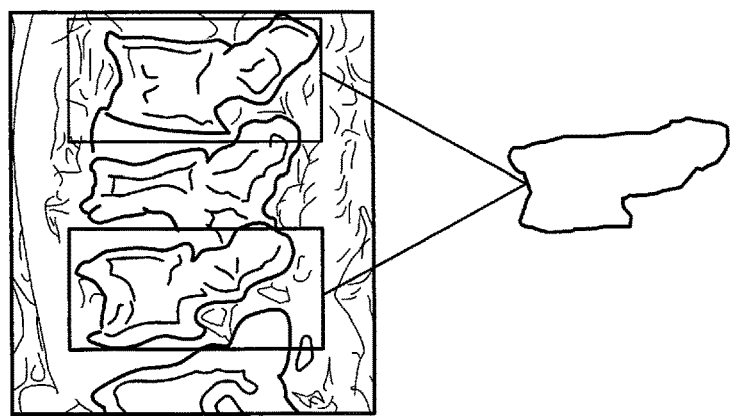
F I G. 7

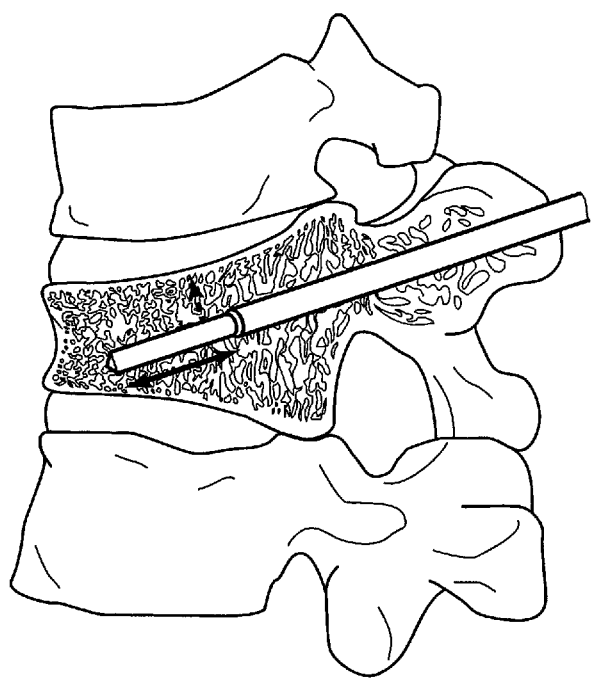
F I G. 8
F I G. 9

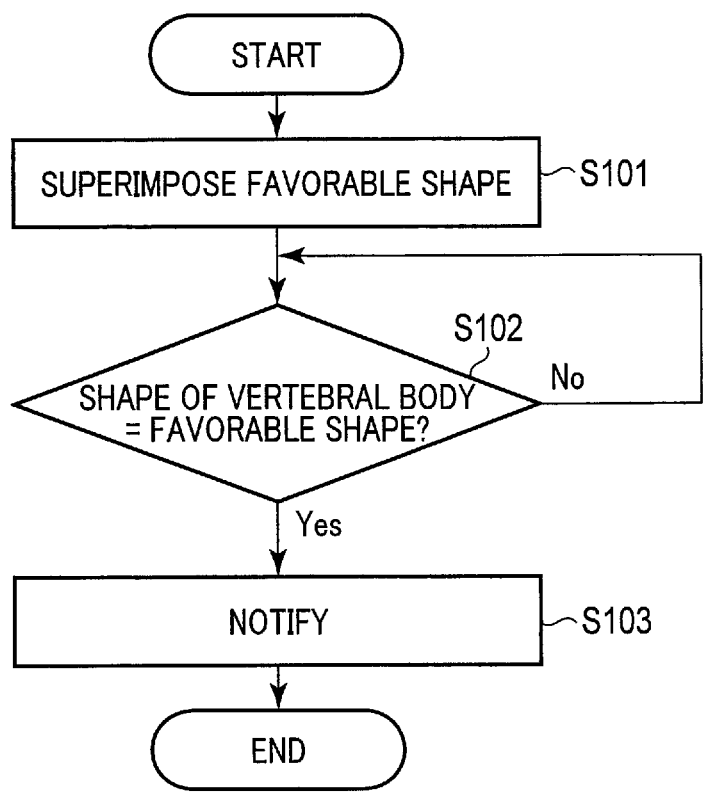
F I G. 10
F I G. 11

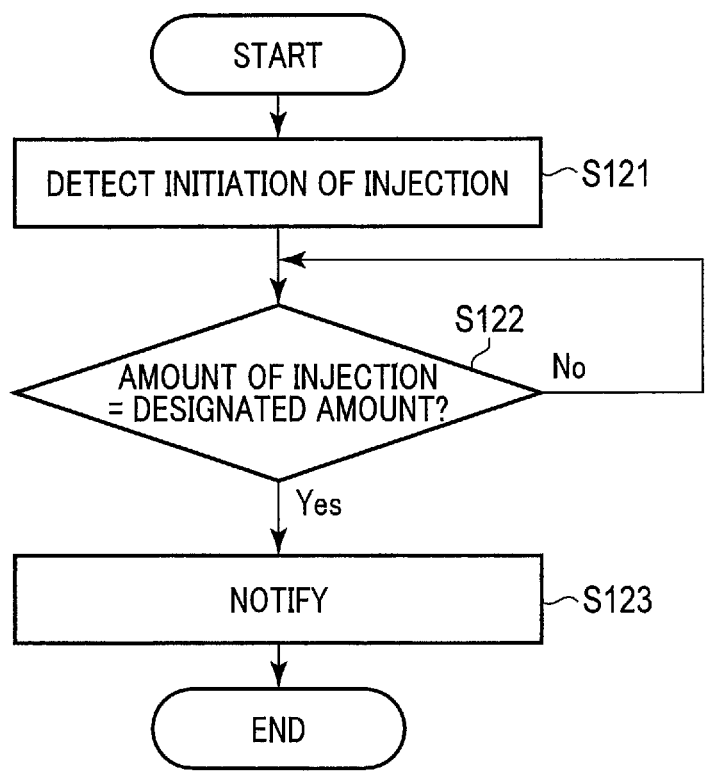
F I G. 12

SUPPORT INFORMATION-GENERATION APPARATUS, WARNING INFORMATION-NOTIFICATION APPARATUS, AND SUPPORT INFORMATION-GENERATION METHOD

CROSS-REFERENCE TO RELATED APPLICATIONS

This application is based upon and claims the benefit of priority from the prior Japanese Patent Application No. 2018-075421, filed Apr. 10, 2018, the entire contents of which is incorporated herein by reference.

FIELD

Embodiments described herein relate generally to a support information-generation apparatus, a warning information-notification apparatus, and a support information generation method.

BACKGROUND

As a conventional art, there is a method called balloon kyphoplasty (BKP) for treating a compression fracture of a vertebral body. The BKP is one type of percutaneous vertebroplasty. In the BKP treatment, a path to the interior of a fractured vertebral body is created. A balloon is inserted into the vertebral body through the path and inflated inside the vertebral body, so that the vertebral body returns to its original shape before the fracture. The balloon is then deflated and removed. Bone cement is injected into a cavity expanded by the balloon, so that the vertebral body is fixated in its original shape prior to the fracture.

The BKP treatment is performed under X-ray fluoroscopy to guide a treatment tool into the vertebral body. However, the state of the inflation of the balloon and the state of the injection of the bone cement are hard to ascertain under X-ray fluoroscopy. Therefore, the balloon may rupture due to excessive injection of a medium, and the bone cement may leak into the exterior of the vertebral body due to excessive injection of the bone cement.

BRIEF DESCRIPTION OF THE DRAWINGS

FIG. 5 is a diagram showing a sectional image of a backbone, as viewed in the cross section along A-A' illustrated in FIG. 4.

FIG. 6 is a diagram illustrating an example of displaying a surface image of the vertebral body region.

FIG. 7 is a diagram illustrating an example of obtaining a shape in a favorable condition of the vertebral body targeted for treatment.

FIG. 8 is a diagram illustrating an example of a simulation of a state in which a needle is inserted into a determined path.

FIG. 9 is a diagram illustrating an example of a perspective image displayed on a display illustrated in FIG. 1.

FIG. 10 is a flowchart of an operation for guiding the injection of a medium into a balloon via processing circuitry of an image-processing apparatus illustrated in FIG. 1.

FIG. 11 is a diagram illustrating an example of displaying an image of the shape of the vertebral body in a favorable condition superimposed on the vertebral body in the perspective image.

FIG. 12 is a flowchart of an operation for guiding injection of bone cement into the vertebral body via the processing circuitry of the image-processing apparatus illustrated in FIG. 1.

DETAILED DESCRIPTION

In general, according to one embodiment, a support information-generation apparatus includes processing circuitry. The processing circuitry extracts a vertebral body region from a medical image obtained before surgery and calculates a first volume of a vertebral body targeted for treatment by percutaneous vertebroplasty based on the extracted vertebral body region. The processing circuitry estimates a second volume of the targeted vertebral body related to an estimated shape after the treatment. The processing circuitry calculates, based on a difference between the first volume and the second volume, a volume of an object to be inserted so as to deform the targeted vertebral body into the estimated shape.

Embodiments will be described below with reference to the drawings.

First Embodiment

Figure 1:
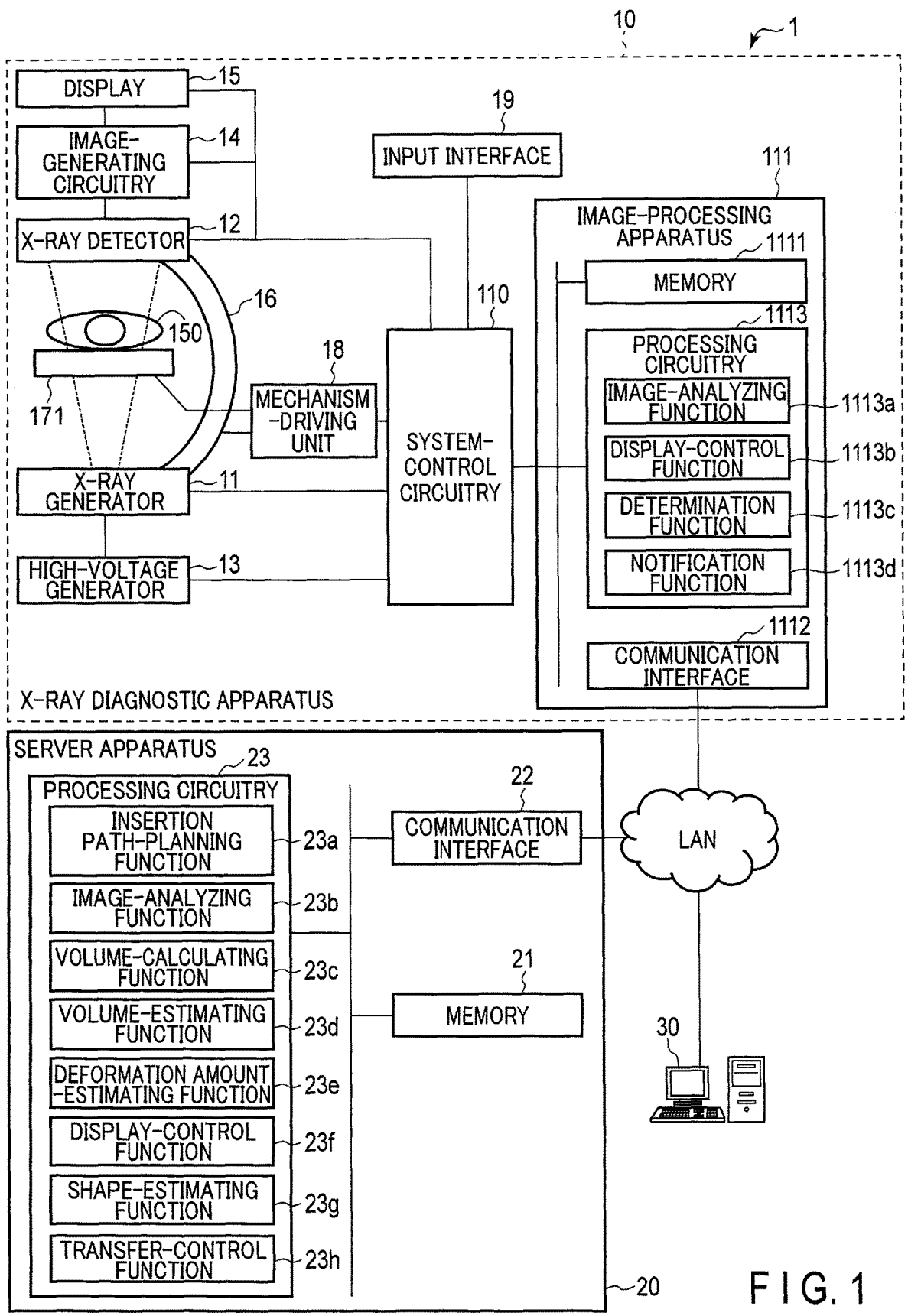
FIG. 1 is a block diagram illustrating a functional configuration of a support information-generation apparatus according to a first embodiment.

FIG. 1 is a block diagram illustrating an example of a functional configuration of a support information-generation apparatus 1 according to a first embodiment. The support information-generation apparatus 1 illustrated in FIG. 1 includes an X-ray diagnostic apparatus 10, a server apparatus 20, and a communication terminal 30. FIG. 1 illustrates an example in which the balloon kyphoplasty (BKP) treatment is performed using the X-ray diagnostic apparatus 10.

The X-ray diagnostic apparatus 10, the server apparatus 20, and the communication terminal 30 are connected to one another via an in-hospital network, such as a local area network (LAN), to allow for data communication. The connection to the in-hospital network may be made either by wire or wirelessly. Also, a connected line is not limited to the in-hospital network as long as security is ensured. For example, the devices may be connected to the public communication lines, such as the Internet, via a virtual private network (VPN).

The server apparatus 20 illustrated in FIG. 1 generates, by simulation, information for supporting the BKP treatment performed using the X-ray diagnostic apparatus 10. The server apparatus 20 is, for example, one of the server apparatuses that form a radiological information system (RIS). The server apparatus 20 illustrated in FIG. 1 includes a memory 21, a communication interface 22, and processing circuitry 23. The memory 21, the communication interface 22, and the processing circuitry 23 are connected to one another via a bus, for example, to be able to communicate with one another.

The memory 21 includes, for example, a magnetic or optical storage medium, or a processor-readable storage medium such as a semiconductor memory. The memory 21 stores, for example, a support information-generation program according to the present embodiment. For example, the support information-generation program may be stored in advance in the memory 21, or may be stored in the memory 21 after being stored in a non-transitory storage medium, distributed, and then read from the non-transitory storage medium. Also, the support information-generation program may be stored in the memory 21 after being transmitted from an external apparatus such as another server apparatus.

The memory 21 also stores medical image data regarding a medical image obtained by a medical diagnostic imaging apparatus such as magnetic resonance imaging (MRI) apparatus or an X-ray computed tomography (CT) apparatus. The medical image data is read from, for example, a medical image management system (PACS: picture archiving and communication system) via the communication interface 22. At this time, standards compliant with digital imaging and communication medicine (DICOM), for example, are used for the communication with the medical image management system.

The memory 21 stores, for example, data generated by the processing circuitry 23. The data generated by the processing circuitry 23 includes, for example, data related to a path of a needle inserted into a vertebral body targeted for the BKP treatment and data related to an amount of deformation of the vertebral body during the treatment. The data generated by the processing circuitry 23 may include, for example, data related to a shape in a favorable condition of the vertebral body targeted for the BKP treatment.

The memory 21 may be, for example, a drive device configured to read and write various kinds of information from and to a portable storage medium. At this time, the data generated by the processing circuitry 23 may be, for example, written to the portable storage medium, so that the portable storage medium is passed to a doctor in charge of the BKP treatment. The memory 21 does not necessarily have to be implemented by a single storage device. For example, the memory 21 may be implemented by a plurality of storage devices. Also, the memory 21 may be arranged in another computer connected to the server apparatus 20 via a network.

The communication interface 22 performs data communication with the X-ray diagnostic apparatus 10 and the communication terminal 30 connected to the communication interface 22 via the in-hospital network. For example, the communication interface 22 performs data communication in accordance with the preset known standards.

The server apparatus 20 may include an input interface. The input interface receives various types of input operations from a user, converts the received input operations to an electric signal, and outputs the electric signal to the processing circuitry 23. The input interface is connected to input devices such as a mouse, a keyboard, a trackball, a switch, a button, a joystick, a touch pad, and a touch panel to which instructions are input by a touch on its operation screen. The input devices connected to the input interface may be input devices provided to another computer connected via a network, etc.

The server apparatus 20 may also include a display. The display displays various kinds of information according to instructions from the processing circuitry 23. The display may also display, for example, a graphical user interface (GUI) for receiving various types of operations from a user. The display may be any suitably employed display, such as a cathode ray tube (CRT) display, a liquid crystal display, an organic EL display, an LED display, or a plasma display.

The processing circuitry 23 is a processor functioning as a main unit of the server apparatus 20. The processing circuitry 23 executes a program stored in the memory 21, etc., to thereby accomplish functions corresponding to the program. The processing circuitry 23 executes the support information-generation program stored in the memory 21 to thereby accomplish functions corresponding to the program. For example, the processing circuitry 23, by executing the support information-generation program, has an insertion path-planning function 23a, an image-analyzing function 23b, a volume-calculating function 23c, a volume-estimating function 23d, a deformation amount-estimating function 23e, a display-control function 23f, a shape-estimating function 23g, and a transfer-control function 23h. In the present embodiment, a case is described where the insertion path-planning function 23a, the image-analyzing function 23b, the volume-calculating function 23c, the volume-estimating function 23d, the deformation amount-estimating function 23e, the display-control function 23f, the shape-estimating function 23g, and the transfer-control function 23h are fulfilled by a single processor; however, the present embodiment is not limited thereto. For example, a plurality of independent processors may be combined to form processing circuitry, so that each of the processors executes the program to thereby fulfill the insertion path-planning function 23a, the image-analyzing function 23b, the volume-calculating function 23c, the volume-estimating function 23d, the deformation amount-estimating function 23e, the display-control function 23f, the shape-estimating function 23g, and the transfer-control function 23h. The insertion path-planning function 23a is a function to plan a path for the insertion of a needle into a vertebral body. Specifically, with the insertion path-planning function 23a, for example, the processing circuitry 23 presents, to an operator, a medical image regarding a patient scheduled for surgery based on the medical image data stored in the memory 21. The processing circuitry 23 determines, as the insertion path, a path designated by the operator in the medical image.

The image-analyzing function 23b is a function to analyze the medical image data and extract a vertebral body region from the medical image data. Specifically, with the image-analyzing function 23b, for example, the processing circuitry 23 analyzes the medical image data stored in the memory 21 regarding the patient scheduled for surgery. The processing circuitry 23 extracts a vertebral body region from the medical image data using an existing method such as a region-expansion method.

The volume-calculating function 23c is a function to calculate a volume of the vertebral body targeted for the BKP treatment. Specifically, with the volume-calculating function 23c, for example, the processing circuitry 23 calculates a volume of the vertebral body targeted for the BKP treatment based on the vertebral body region extracted by the image analysis.

The volume-estimating function 23d is a function to estimate a volume in a favorable condition of the vertebral body targeted for the BKP treatment. In this embodiment, the favorable condition refers to a condition of the vertebral body before deformation, i.e., a condition of the vertebral body before compression fracture. With the volume-estimating function 23d, the processing circuitry 23, for example, calculates volumes of vertebral bodies positioned above and below the vertebral body targeted for the BKP treatment based on the vertebral body region extracted by the image analysis. The processing circuitry 23 estimates a volume in a favorable condition of the vertebral body targeted for the BKP treatment based on the calculated volumes of the upper and lower vertebral bodies.

The deformation amount-estimating function 23e is a function to estimate a volume of the vertebral body targeted for the BKP treatment to be deformed in the BKP treatment. Specifically, with the deformation amount-estimating function 23e, for example, the processing circuitry 23 subtracts the volume of the vertebral body region extracted by the image analysis from the volume of the vertebral body in a favorable condition, to thereby calculate a volume of the vertebral body to be deformed. Calculation of the volume of the vertebral body to be deformed may also be expressed as calculation of the volume of an object to be inserted so as to deform the vertebral body into a favorable condition.

The display-control function 23f is a function to present information related to the estimated deformation amount to the operator. Specifically, with the display-control function 23f, for example, the processing circuitry 23 presents an amount of inflation of a balloon and an amount of injection of bone cement to the operator via the communication terminal 30 based on the estimated deformation amount.

The shape-estimating function 23g is a function to estimate a shape in a favorable condition of the vertebral body targeted for the BKP treatment. Specifically, with the shape-estimating function 23g, for example, the processing circuitry 23 estimates a shape in a favorable condition of the vertebral body targeted for the BKP treatment based on the vertebral body regions of the vertebral bodies positioned above and below the vertebral body targeted for the BKP treatment extracted by the image analysis.

The transfer-control function 23h is a function to transfer the data generated by the processing circuitry 23 to the X-ray diagnostic apparatus 10. Specifically, with the transfer-control function 23h, for example, the processing circuitry 23 transfers, to the X-ray diagnostic apparatus 10, the data related to the path of the needle inserted into the vertebral body targeted for the BKP treatment, the data related to the amount of deformation of the vertebral body during the treatment, and the data related to the shape of the vertebral body in a favorable condition.

Figure 2:
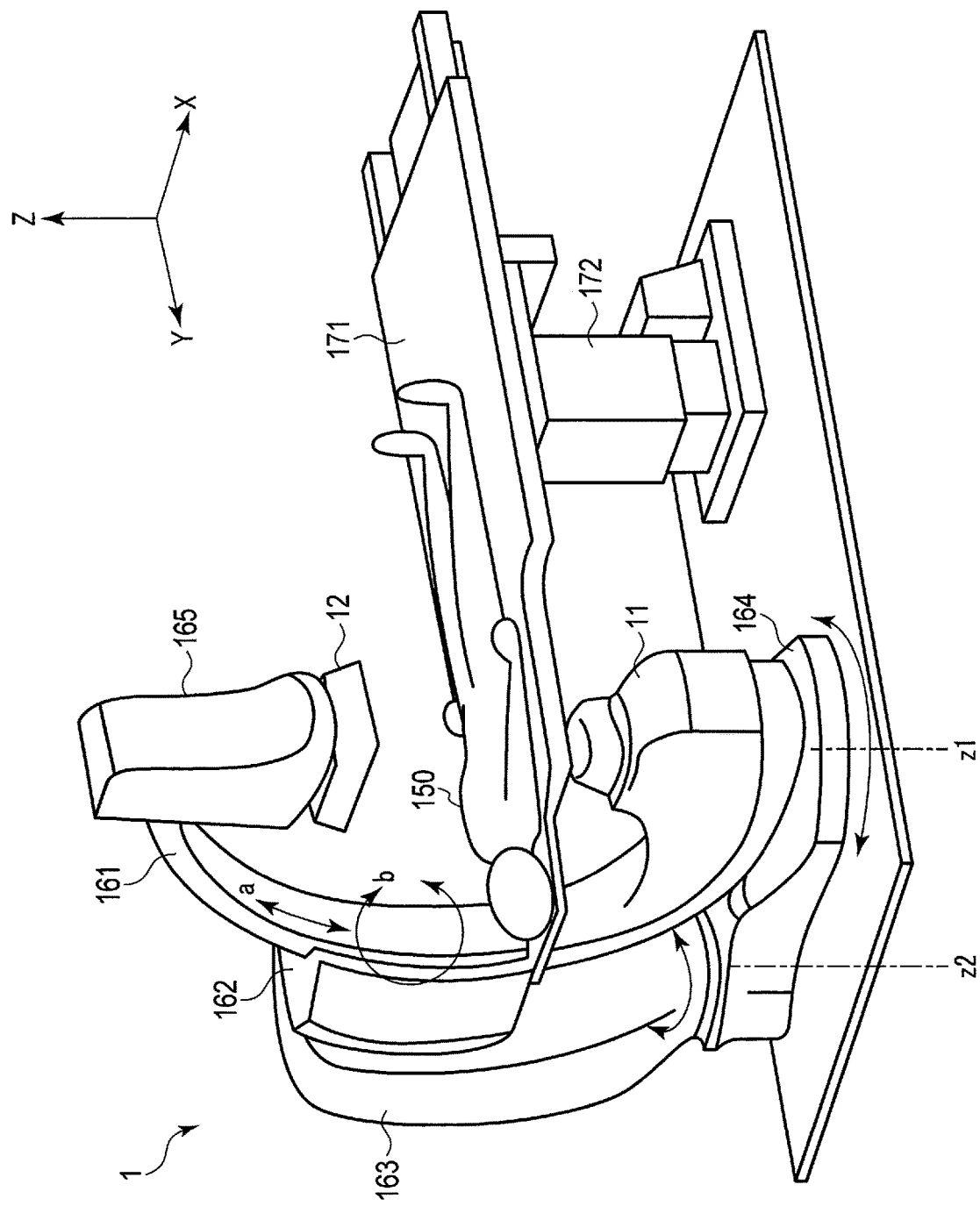
FIG. 2 is a diagram illustrating an external appearance of an X-ray diagnostic apparatus illustrated in FIG. 1.

FIG. 2 is a schematic diagram illustrating an example of an external appearance of the X-ray diagnostic apparatus 10 illustrated in FIG. 1. FIG. 2 illustrates an example in which a holding device 16 of the X-ray diagnostic apparatus 10 includes a floor-positioned C-arm 161 whose ends are attached to an X-ray generator 11 and an X-ray detector 12; however, the present embodiment is not limited thereto. For example, the holding device 16 may be a ceiling-hung C-arm or Q-shaped arm.

The X-ray diagnostic apparatus 10 illustrated in FIG. 1 includes the X-ray generator 11, the X-ray detector 12, a high-voltage generator 13, image-generating circuitry 14, a display 15, the holding device 16, a bed unit 17, a mechanism-driving unit 18, an input interface 19, system-control circuitry 110, and an image-processing apparatus 111.

The X-ray generator 11 is provided on one end of the C-arm 161, and generates X-rays to be radiated to a subject 150 on a top plate 171. The X-ray generator 11 includes an X-ray tube and an X-ray narrowing device that forms an X-ray cone beam of the X-rays radiated from the X-ray tube. The X-ray tube, which is a vacuum tube that generates X-rays, generates X-rays by accelerating electrons released from a cathode (filament) using a high voltage and causing the electrons to collide with a tungsten anode. The X-ray narrowing device is positioned between the X-ray tube and the subject 150, and narrows the X-ray beams radiated from the X-ray tube down to a predetermined irradiation view size.

The X-ray detector 12 is attached to a detector forward-and-backward motion unit 165 in a manner to face the X-ray generator 11, and detects the X-rays transmitted through the subject 150. The X-ray detector 12 is implemented by, for example, a flat-panel detector having a plurality of X-ray detection semiconductor elements that are arranged two-dimensionally. The detector forward-and-backward motion unit 165 is attached to the other end of the C-arm 161 so as to be able to move back and forth along a direction toward the X-ray generator 11.

The high-voltage generator 13 includes: a high-voltage generator configured to generate a high voltage to be applied between an anode and a cathode in order to accelerate thermoelectrons generated from the cathode of the X-ray tube; and an X-ray controller configured to control X-ray irradiation conditions, such as a tube current and a tube voltage of the high-voltage generator, irradiation time, and irradiation timing, according to an instruction signal supplied from the system-control circuitry 110.

The image-generating circuitry 14 includes a projection data-generating circuitry, a projection data memory circuitry, and an image-computing circuitry, which are not shown in the figure. The projection data-generating circuitry includes: a charge-voltage converter configured to convert, into a voltage, electric charges read in parallel from the flat-panel detector in a unit of row or a unit of column; an A/D converter configured to convert an output of the charge-voltage converter into a digital signal; and a parallel-serial converter configured to convert, into a time-series serial signal, a parallel signal converted into a digital signal. The projection data-generating circuitry supplies this serial signal to the projection data memory circuitry as time-series projection data. The projection data memory circuitry sequentially stores the time-series projection data supplied from the projection data-generating circuitry and generates two-dimensional projection data. The image computing circuitry performs image processing, such as filtering, on the two-dimensional projection data generated by the projection data memory circuitry and generates perspective image data.

In accordance with an instruction from the system-control circuitry 110, the display 15 superimposes supplementary information, such as subject information and conditions of generating the projection data, on the perspective image data supplied from the image-generating circuitry 14, and generates display data. The display 15 displays the generated display data after performing D/A conversion and TV format conversion thereon. Any display, such as a cathode ray tube (CRT) display, a liquid crystal display, an organic EL display, an LED display, or a plasma display, may be suitably employed as the display 15.

The holding device 16 holds the X-ray generator 11 and the X-ray detector 12 in a manner that makes the X-ray generator 11 and the X-ray detector 12 rotatable, and moves or turns the X-ray generator 11 and the X-ray detector 12 in a predetermined direction around the subject 150 according to a drive signal from the mechanism-driving unit 18. The holding device 16 according to the present embodiment includes, for example, the C-arm 161, a C-arm holder 162, a stand 163, and a floor-pivoting arm 164.

The C-arm 161 holds the X-ray generator 11 and the detector forward-and-backward motion unit 165 so that the X-ray generator 11 and the X-ray detector 12 face each other. The C-arm 161 is held by the stand 163 via the C-arm holder 162. The C-arm holder 162 holds the C-arm 161 slidably in a direction of an arc of the C-arm 161, i.e., the direction indicated by arrow a in FIG. 2. The C-arm holder 162 is attached to the stand 163 so as to pivot about an axis perpendicular to a pivot axis z2 of the stand 163, e.g., the direction indicated by arrow b. As the C-arm holder 162 pivots in direction b, the C-arm 161 pivots in direction b.

The stand 163 is attached to the floor-pivoting arm 164 so as to pivot about the pivot axis z2. The stand 163 supports the C-arm holder 162 in a direction perpendicular to the pivot axis z2. One end of the floor-pivoting arm 164 is attached to a floor surface so as to pivot about a pivot axis z1. Another end of the floor-pivoting arm 164 supports the stand 163. The pivot axes z1 and z2 extend in the same direction perpendicular to the floor.

The bed unit 17 is configured to move the top plate 171 with the subject 150 thereon in a predetermined direction according to a drive signal from the mechanism-driving unit 18. A bed 172 of the bed unit 17 is provided with a horizontal movement mechanism for moving the top plate 171 with the subject 150 thereon in a horizontal direction, and a vertical movement mechanism for moving the top plate 171 with the subject 150 thereon in a vertical direction.

The mechanism-driving unit 18 is controlled by the system-control circuitry 110 and supplies a drive signal to each of the holding device 16 and the bed unit 17. Specifically, the mechanism-driving unit 18 supplies a drive signal to the holding device 16 to move the X-ray generator 11 and the X-ray detector 12 in a desired direction. By detecting the drive signal supplied to the holding device 16 (e.g., counting a drive pulse number), the system-control circuitry 110 can detect positional information of an imaging system. Also, the mechanism-driving unit 18 supplies a drive signal to the bed 172 to move the top plate 171 with the subject 150 thereon in a desired direction. By detecting the drive signal supplied to the bed 172, the system-control circuitry 110 can detect positional information of the top plate 171.

The input interface 19 receives various instructions from an operator. Examples of the various instructions include an instruction of inputting subject information, an instruction of setting conditions of X-ray photography including X-ray irradiation conditions, and an instruction of inputting various command signals. The input interface 19 is implemented by, for example, a mouse, a keyboard, a panel switch, a slider switch, a trackball, a rotary encoder, an operation panel, and a touch command screen (TCS). The input interface 19 is connected to the system-control circuitry 110, for example, via a bus. The input interface 19 converts an operation instruction input by the operator into an electric signal, and outputs the electric signal to the system-control circuitry 110. In the present embodiment, the input interface 19 is not limited to one that includes physical operation components such as a mouse and a keyboard. For example, circuitry configured to receive an electric signal corresponding to an operation instruction input from an external input device provided separately from an apparatus, and output the electric signal to the system-control circuitry 110, is also included as an example of the input interface 19.

The system-control circuitry 110 is, for example, a processor for comprehensively controlling the X-ray diagnostic apparatus 10. The system-control circuitry 110 includes a memory (not shown), and stores a program for controlling the X-ray diagnostic apparatus 10 in the memory. The system-control circuitry 110 stores, in the memory, subject information input using the input interface 19, various command signals, and conditions of X-ray photography set using the input interface 19. The system-control circuitry 110 executes a control program stored in the memory using the information stored in the memory, to thereby comprehensively control the X-ray diagnostic apparatus 10.

The image-processing apparatus 111 supports the operator while the BKP treatment is performed. The image-processing apparatus 111 includes a memory 1111, a communication interface 1112, and processing circuitry 1113.

The memory 1111 includes, for example, a magnetic or optical storage medium, or a processor-readable storage medium such as a semiconductor memory. The memory 1111 stores, for example, a support information-generation program according to the present embodiment. For example, the support information-generation program may be stored either in advance in the memory 1111, or in the memory 1111 after being stored in a non-transitory storage medium, distributed, and then read from the non-transitory storage medium. Also, the support information-generation program may be stored in the memory 1111, for example, after being transmitted from an external apparatus such as the server apparatus 20.

The memory 1111 stores, for example, the perspective image data generated by the image-generating circuitry 14 and data generated by the server apparatus 20. The data generated by the server apparatus 20 includes, for example, data related to a path of a needle inserted into a vertebral body targeted for the BKP treatment, and data related to an amount of deformation of the vertebral body during the treatment. Also, the data generated by the server apparatus 20 may include, for example, data related to a shape in a favorable condition of the vertebral body targeted for the BKP treatment. The memory 1111 may be, for example, a drive device configured to read and write various kinds of information from and to a portable storage medium such as a CD-ROM drive, a DVD drive, or a and flash memory. At this time, the memory 1111 may, for example, read data written to a portable storage medium through the server apparatus 20.

The memory 1111 need not necessarily be implemented by separate storage devices. For example, the memory 1111 may be implemented by a plurality of storage devices. The memory 1111 may be implemented by the same storage device as that of the memory 21 of the server apparatus 20.

The communication interface 1112 is connected to the server apparatus 20 and the communication terminal 30 via an in-hospital network, and performs data communication with the server apparatus 20 and the communication terminal 30.

The processing circuitry 1113 is, for example, processor functioning as a main unit of the image-processing apparatus 111. The processing circuitry 1113 executes a control program stored in the memory 1111 to thereby accomplish functions corresponding to the program. The processing circuitry 1113 has, for example, an image-analyzing function 1113a, a display-control function 1113b, a determination function 1113c, and a notification function 1113d. In the present embodiment, a case where the image-analyzing function 1113a, the display-control function 1113b, the determination function 1113c, and the notification function 1113d are fulfilled by a single processor is described; however, the present embodiment is not limited thereto. For example, a plurality of independent processors may be combined to form processing circuitry, so that each of the processors executes the program to thereby fulfill the image-analyzing function 1113a, the display-control function 1113b, the determination function 1113c, and the notification function 1113d.

The image-analyzing function 1113a is a function to analyze the perspective image data generated by the image-generating circuitry 14. Specifically, with the image-analyzing function 1113a, for example, the processing circuitry 1113 analyzes the perspective image data generated by the image-generating circuitry 14. The processing circuitry 1113 extracts a vertebral body region from the perspective image data using an existing method such as a region expansion method.

The display-control function 1113b is a function to control the display of the perspective image data by the display 15. Specifically, with the display-control function 1113b, for example, the processing circuitry 1113 displays, on the display 15, a perspective image based on the perspective image data generated by the image-generating circuitry 14. The processing circuitry 1113 superimposes a display regarding an intraoperative guide on the perspective image. Specifically, the processing circuitry 1113, for example, superimposes, onto the perspective image, a guide display for determining a position of the holding device 16 and a position of the bed unit 17 for the BKP treatment, and a guide display for guiding a needle into the vertebral body targeted for the BKP treatment. The processing circuitry 1113 superimposes a favorable shape of the vertebral body targeted for treatment onto the perspective image.

The determination function 1113c is a function to determine whether or not an inflation of a balloon is sufficient and whether or not an amount of injection of bone cement into the vertebral body is sufficient. Specifically, with the determination function 1113c, for example, the processing circuitry 1113 compares a shape of the vertebral body presented in the perspective image with a favorable shape superimposed onto the vertebral body in the perspective image. If the actual shape of the vertebral body substantially matches the favorable shape, the processing circuitry 1113 determines that the balloon has inflated sufficiently.

The processing circuitry 1113 determines whether or not an amount of bone cement injected into the vertebral body matches an amount of bone cement calculated in a preoperative simulation performed by the server apparatus 20. If the amount of bone cement injected matches the amount of bone cement calculated, the processing circuitry 1113 determines that bone cement has been injected sufficiently.

The notification function 1113d is a function to notify that the inflation of the balloon is sufficient and that the amount of injection of bone cement into the vertebral body is sufficient. Specifically, with the notification function 1113d, for example, when the inflation of the balloon is sufficient, the processing circuitry 1113 notifies the operator of that. Also, when the amount of injection of bone cement into the vertebral body is sufficient, the processing circuitry 1113 notifies the operator of that. The notification to the operator may be made by sound or displayed by the display 15.

The communication terminal 30 illustrated in FIG. 1 is a terminal for medical staff, such as doctors, accessing the server apparatus 20, etc., via the in-hospital network. The number of communication terminals 30 accommodated in the in-hospital network is not limited to one. A plurality of communication terminals 30 may be accommodated in the in-hospital network. If the server apparatus 20 includes an input interface and a display, the communication terminal 30 need not necessarily be installed.

Next, an operation for supporting the BKP treatment by the support information-generation apparatus 1 having the above-described configuration will be described.

(Preoperative Simulation)

Figure 3:
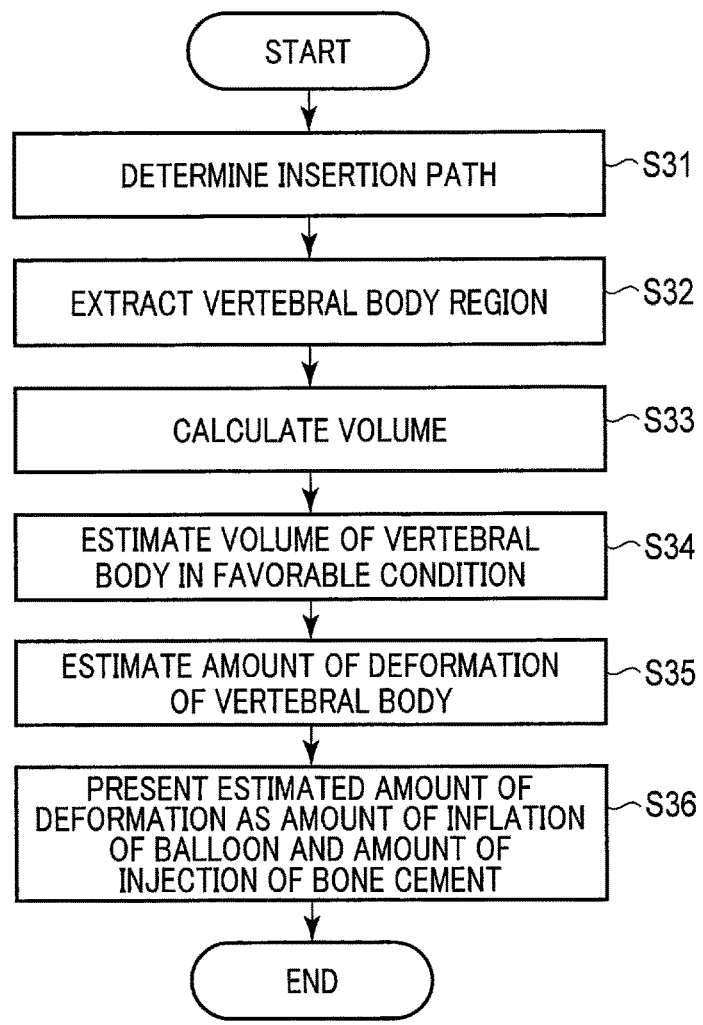
FIG. 3 is a flowchart of an operation for performing a preoperative simulation by processing circuitry of a server apparatus illustrated in FIG. 1.

A case where the server apparatus 20 performs a preoperative simulation for the BKP treatment will be described. FIG. 3 is a flowchart illustrating an example of an operation for performing a preoperative simulation by the processing circuitry 23 of the server apparatus 20 illustrated in FIG. 1.

First, the operator checks a schedule for the BKP treatment through the communication terminal 30. Based on the time and date, patient ID, patient information, etc., the operator specifies the BKP treatment for which the preoperative simulation is performed. The operator inputs an instruction for starting the preoperative simulation of the specified BKP treatment to the server apparatus 20. Upon receiving the instruction for starting the preoperative simulation, the processing circuitry 23 of the server apparatus 20 reads the support information-generation program from the memory 21 and executes the read support information-generation program.

Via the execution of the support information-generation program, the processing circuitry 23 performs the insertion path-planning function 23a. By performing the insertion path-planning function 23a, the processing circuitry 23 determines a path for the insertion of a needle into a vertebral body (step S31). Specifically, the processing circuitry 23 reads, from the PACS, CT image data of a backbone of a designated patient captured before surgery, or medical image data of MR image data, and stores the read medical image data in the memory 21. The medical image data to be read at this time includes, for example, at least a vertebral body designated as a treatment target by a doctor who examined the patient, and vertebral bodies positioned above and below the vertebral body designated as a treatment target. The processing circuitry 23 displays an axial sectional image of the vertebral body targeted for treatment on the communication terminal 30 in response to designation of an axial cross section by the operator.

Figure 4:
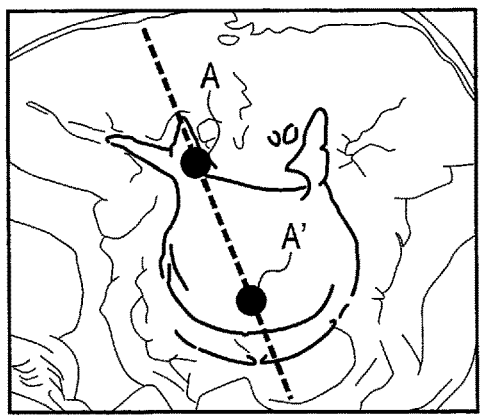
FIG. 4 is a diagram showing an axial sectional image of a vertebral body targeted for treatment.

FIG. 4 is a schematic diagram illustrating an example of displaying the axial sectional image of the vertebral body targeted for treatment. The operator designates a path for the insertion of a needle based on the axial sectional image shown in FIG. 4. For example, the operator designates two points in the axial sectional image. The processing circuitry 23 determines the straight line connecting the two designated points A and A' as a path for the insertion of a needle. The processing circuitry 23 stores, in the memory 21, data related to the insertion path determined, such as positional information of the insertion path and a transverse puncture angle.

The processing circuitry 23 may also determine a cephalocaudal puncture angle. The cephalocaudal puncture angle needs to be determined, for example, when the spine is badly bent, and the vertebral bodies are badly leaning in the cephalocaudal direction. Specifically, when the two points A and A' are designated, for example, the processing circuitry 23 refers to the medical image data and displays a sectional image of the backbone along the straight line A-A' on the communication terminal 30. FIG. 5 is a schematic diagram illustrating an example of displaying the sectional image of the backbone along the straight line A-A'. The operator determines a cephalocaudal puncture angle based on the sectional image shown in FIG. 5.

Once the processing circuitry 23 determines the path for the insertion of a needle, the processing circuitry 23 performs the image-analyzing function 23b. By performing the image-analyzing function 23b, the processing circuitry 23 performs a predetermined image analysis on the medical image data to thereby extract a vertebral body region included in the medical image data (step S32). Specifically, the processing circuitry 23 performs the processing of extracting a region on the medical image data read in step S31 by using an existing method such as a region expansion method. As a result, three-dimensional information regarding a plurality of vertebral bodies including the vertebral body targeted for treatment, for example, is extracted from the medical image data.

Once the processing circuitry 23 extracts the vertebral body region from the medical image data, the processing circuitry 23 performs the volume-calculating function 23c. By performing the volume-calculating function 23c, the processing circuitry 23 calculates a volume of the vertebral body targeted for treatment (step S33). Specifically, the processing circuitry 23 receives, from the operator, designation of the vertebral body targeted for treatment, for example, with respect to a surface image based on the vertebral body region extracted from the medical image data. Once the vertebral body is designated by the operator, the processing circuitry 23 calculates a volume of the designated vertebral body based on the three-dimensional information of the designated vertebral body such as the number of pixels. FIG. 6 is a diagram illustrating an example of displaying the surface image of the vertebral body region. In the example illustrated in FIG. 6, a central vertebral body is designated by the operator, and the volume of the designated vertebral body is calculated as 7 mm$^3$.

The designation of the vertebral body targeted for treatment by the operator is not a requisite. The processing circuitry 23 may automatically recognize the vertebral body targeted for treatment. For example, the processing circuitry 23 calculates volumes of a plurality of vertebral body regions included in the medical image data. The processing circuitry 23 may select the volume of the vertebral body targeted for treatment based on the relationship among the volumes of the plurality of vertebral body regions calculated. For example, the processing circuitry 23 may determine the smallest volume as the volume of the vertebral body targeted for treatment. Also, a vertebral body whose volume decreases non-sequentially among the vertebral bodies that are aligned may be determined as the vertebral body targeted for treatment, so that the volume of the vertebral body is obtained.

The processing circuitry 23 may select the vertebral body targeted for treatment based on the shape of the vertebral body. For example, the processing circuitry 23 expands the vertebral body region by one voxel and subtracts the vertebral body region before the expansion from the vertebral body region after the expansion, to thereby obtain information on the shape of the vertebral body region. The processing circuitry 23 approximates a fitting curve representing a shape from the obtained information, and obtains, based on the fitting curve, a feature amount such as an inflection point that defines the smoothness. The processing circuitry 23 collates the obtained feature amount with a preset definition of a compression fracture, and detects the vertebral body region having a compression fracture. The definition of the "compression fracture" includes, for example, presence of a preset number or more of inflection points within a predetermined range of about several millimeters, i.e., presence of uneven parts densely formed on the surface of the vertebral body. The processing circuitry 23 calculates the volume of the vertebral body region having a compression fracture.

Once the processing circuitry 23 calculates the volume of the vertebral body targeted for treatment, the processing circuitry 23 performs the volume-estimating function 23d. With the volume-estimating function 23d, the processing circuitry 23 estimates a volume in a favorable condition of the vertebral body targeted for treatment, i.e., a volume of the vertebral body before having a compression fracture (step S34). Specifically, the processing circuitry 23 calculates volumes of vertebral bodies not having a compression fracture, such as vertebral bodies above and below the vertebral body targeted for treatment, based on the three-dimensional information of these vertebral bodies such as the number of pixels. The processing circuitry 23 calculates the volume in a favorable condition of the vertebral body targeted for treatment based on the volumes of the two vertebral bodies calculated. For example, the processing circuitry 23 calculates an average value of the volumes of the two vertebral bodies, and determines the calculated average value as the volume in a favorable condition of the vertebral body targeted for treatment. In the example illustrated in FIG. 6, the volumes of the vertebral bodies above and below the vertebral body designated by the operator are calculated as 10 mm$^3$ and 16 mm$^3$, respectively. Then, the average value 13 mm$^3$ of 10 mm$^3$ and 16 mm$^3$ is calculated as the volume in a favorable condition of the vertebral body targeted for treatment.

A procedure for estimating the volume in a favorable condition of the vertebral body targeted for treatment is not limited to that described above. For example, a volume used for obtaining the volume of the vertebral body targeted for treatment is not limited to the volumes of the upper and lower vertebral bodies. For example, a plurality of vertebral bodies may be selected, or only one vertebral body may be selected. Also, a statistical procedure adopted is not limited to obtaining an average value. For example, a median, a minimum value, and a maximum value of the volumes of the vertebral bodies selected may be adopted as the volume of the vertebral body in a favorable condition.

Additionally, the volume of the vertebral body in a favorable condition may be estimated by referring to known data such as an atlas of a human body. The "volume in a favorable condition" may also be referred to as an estimated volume of the vertebral body after treatment of the compression fracture.

Once the processing circuitry 23 calculates the volume in a favorable condition of the vertebral body targeted for treatment, the processing circuitry 23 performs the deformation amount-estimating function 23e. With the deformation amount-estimating function 23e, the processing circuitry 23 estimates a volume of the vertebral body to be deformed in the BKP treatment (step S35). Specifically, the processing circuitry 23 subtracts the volume of the vertebral body in the present condition from the volume of the vertebral body in a favorable condition, and determines the volume after the subtraction as an amount of deformation of the vertebral body. According to the example illustrated in FIG. 6, the volume of the vertebral body with the compression fracture, which is 7 mm$^3$, is subtracted from the volume of the vertebral body in a favorable condition, which is 13 mm$^3$, so that a value 6 mm$^3$ is determined as an amount of deformation of the vertebral body.

Once the processing circuitry 23 estimates the amount of deformation of the vertebral body, the processing circuitry 23 performs the display-control function 23f. By performing the display-control function 23f, the processing circuitry 23 presents, to the operator via the communication terminal 30, the estimated amount of deformation as a volume of a balloon to be inflated when performing the BKP treatment. The volume of the balloon is equal to a volume of the bone cement to be injected into the vertebral body. The processing circuitry 23 presents, to the operator via the communication terminal 30, the estimated amount of deformation as an amount of injection of the bone cement (step S36).

Also, once the processing circuitry 23 extracts the vertebral body region from the medical image data in step S32, the processing circuitry 23 performs the shape-estimating function 23g. By performing the shape-estimating function 23g, the processing circuitry 23 estimates a shape in a favorable condition of the vertebral body targeted for treatment. The shapes of adjacent vertebral bodies do not vary greatly. Therefore, the shape of the vertebral body targeted for treatment before the compression fracture can be estimated from the shapes of the upper and lower vertebral bodies. For example, the processing circuitry 23 determines, as the vertebral body region in a favorable condition of the vertebral body targeted for treatment, a region obtained by averaging a distribution of the vertebral body regions of the vertebral bodies above and below the vertebral body targeted for treatment. FIG. 7 is a diagram illustrating an example of obtaining the shape in a favorable condition of the vertebral body targeted for treatment.

A procedure for estimating the shape in a favorable condition of the vertebral body targeted for treatment is not limited to that described above. For example, a shape of a vertebral body used for obtaining the shape of the vertebral body targeted for treatment is not limited to the shapes of the upper and lower vertebral bodies. For example, shapes of a plurality of vertebral bodies may be selected, or a shape of only one vertebral body may be selected. Also, a statistical procedure adopted is not limited to obtaining an average value. For example, a median, a minimum value, and a maximum value of the distribution of the vertebral body regions selected may be adopted as the shape of the vertebral body in a favorable condition. Additionally, the shape of the vertebral body in a favorable condition may be estimated by referring to known data such as an atlas of a human body.

The shape of the vertebral body in a favorable condition estimated by the processing circuitry 23 is not limited to three-dimensional information. The processing circuitry 23 may estimate the shape of the vertebral body in a favorable condition in the form of two-dimensional information. For example, among the pieces of information related to the vertebral body regions of the vertebral bodies above and below the vertebral body targeted for treatment, the processing circuitry 23 obtains the information with respect to the cross section along A-A', designated when the path for the insertion of a needle is determined. The processing circuitry 23 determines, as the vertebral body region in a favorable condition of the vertebral body targeted for treatment, a region obtained by averaging a two-dimensional distribution of the upper and lower vertebral body regions.

If the operator is to draw a favorable shape of the vertebral body by himself, or herself, while performing the BKP treatment using the X-ray diagnostic apparatus 10, the shape-estimating function 23g need not be performed.

Once the preoperative simulation ends, the processing circuitry 23 performs the transfer-control function 23h. By performing the transfer-control function 23h, the processing circuitry 23 transfers, to the X-ray diagnostic apparatus 10, the data related to the insertion path set by the insertion path-planning function 23a, the data related to the amount of deformation of the vertebral body estimated by the deformation amount-estimating function 23e, and the data related to the shape of the vertebral body in a favorable condition estimated by the shape-estimating function 23g.

In the manner described above, the processing circuitry 23 of the server apparatus 20 extracts the vertebral body region from the medical image, and calculates the volume of the vertebral body targeted for treatment based on the extracted vertebral body region. The processing circuitry 23 estimates a volume in a normal condition of the vertebral body targeted for treatment based on the extracted vertebral body region. The processing circuitry 23 estimates, from the difference between the calculated volume and the estimated volume, the volume of the vertebral body targeted for treatment that is to be deformed. Thereby, the processing circuitry 23 can estimate the amount of deformation of the vertebral body by the treatment through the preoperative simulation.

Also, once the processing circuitry 23 estimates the amount of deformation of the vertebral body, the processing circuitry 23 presents the estimated amount of deformation to the operator as the amount of inflation of the balloon and/or the amount of injection of the bone cement. Thereby, the processing circuitry 23 can recognize in advance the amount of inflation of the balloon and/or the amount of injection of the bone cement through the preoperative simulation.

Also, the processing circuitry 23 estimates the shape of the vertebral body in a favorable condition based on the vertebral body region extracted from the medical image data. This allows the display 15 of the X-ray diagnostic apparatus 10 to more accurately display, during the surgery, the shape in a favorable condition of the vertebral body targeted for treatment.

Also, the processing circuitry 23 determines the path for the insertion of a needle into the vertebral body based on the designation input with respect to the vertebral body region included in the medical image data. This allows the display 15 of the X-ray diagnostic apparatus 10 to display, during the surgery, a guide for determining the positions of the holding device 16 and the bed unit 17 and a guide for inserting a needle into the vertebral body.

The information presented to the operator through the preoperative simulation is not limited to the amount of inflation of the balloon and/or the amount of injection of the bone cement. The processing circuitry 23 may function to present a balloon having an optimal size in the preoperative simulation. At this time, the processing circuitry 23, for example, functions to select a balloon by executing the support information-generation program.

With the balloon-selecting function, the processing circuitry 23 selects, for example, a balloon suited to the size of the vertebral body. If an inflated balloon is too close to an inner wall of a cortical bone of a vertebral body, there is an increased risk of the leakage of the bone cement. Therefore, the processing circuitry 23 selects a balloon based on the maximum balloon diameter and the balloon length described in balloon specifications. Specifically, once the insertion path is determined, for example, the processing circuitry 23 performs the balloon-selecting function. Assuming a state in which a needle is inserted into the determined path, the processing circuitry 23 calculates a length of the needle in the vertebral body and the shortest distance from the needle to the inner wall of the cortical bone. FIG. 8 is a schematic diagram illustrating an example of a simulation of the state in which a needle is inserted into the determined path. In FIG. 8, the solid line represents the length of the needle in the vertebral body, and the broken line represents the shortest distance from the needle to the inner wall of the cortical bone. The processing circuitry 23 selects, as an optimal balloon, a balloon having a balloon length that is smaller than the length of the needle in the vertebral body, and a maximum balloon diameter that is smaller than twice the shortest distance from the needle to the inner wall of the cortical bone. Via the display-control function 23f, the processing circuitry 23 presents the selected balloon to the operator. Thereby, the processing circuitry 23 can present the balloon suited to the size of the vertebral body to the operator.

(Intraoperative Guide)

Next, a case where the X-ray diagnostic apparatus 10 performs an intraoperative guide for the operator who performs the BKP treatment will be described.

Once the BKP treatment is started, the operator inputs an operation command to the input interface 19 so that the display 15 displays a perspective image of a vertebral bone, including a damaged vertebral body of the subject 150. Based on the input of a command indicating a position to capture an image, the system-control circuitry 110 controls the mechanism-driving unit 18 to generate a drive signal to be supplied to the holding device 16 and the bed unit 17. In accordance with the drive signal supplied from the mechanism-driving unit 18, the holding device 16 moves and turns the X-ray generator 11 and the X-ray detector 12 around the subject 150. The bed unit 17 moves the top plate 171 in accordance with the drive signal supplied from the mechanism-driving unit 18. The X-rays generated by the X-ray generator 11 pass through the subject 150 and are detected by the X-ray detector 12. The image-generating circuitry 14 generates perspective image data based on the X-rays detected by the X-ray detector 12. The perspective image data is displayed on the display 15 in the form of a perspective image.

Also, once the BKP treatment is started, the processing circuitry 1113 of the image-processing apparatus 111 reads the support information-generation program from the memory 1111 and executes the read support information-generation program.

By the execution of the support information-generation program, the processing circuitry 1113 performs the display-control function 1113b. Once the processing circuitry 1113 executes the display-control function 1113b, the processing circuitry 1113 superimposes the guide display for performing the BKP treatment onto the perspective image. Specifically, the processing circuitry 1113, for example, reads data related to the path for the insertion of a needle from the memory 1111. The processing circuitry 1113 generates a guide display for determining the positions of the holding device 16 and the bed unit 17 based on the position, etc., of the cross section along A-A' included in the read data. The processing circuitry 1113 superimposes the generated guide display on the perspective image displayed on the display 15.

Once the positions of the holding device 16 and the bed unit 17 are determined according to the guide display superimposed on the perspective image, the perspective image including the cross section along A-A' illustrated in FIG. 9, for example, is displayed on the display 15. Once the positions of the holding device 16 and the bed unit 17 are determined, the processing circuitry 1113 generates a guide display for guiding a needle into the vertebral body based on, for example, the positions of point A and point A' included in the read data. The processing circuitry 1113 superimposes the generated guide display on the perspective image displayed on the display 15.

While checking the perspective image and the guide display superimposed onto the perspective image, the operator guides the needle to reach a pedicle of a vertebral arch and makes the needle advance into the vertebral body. Using a set of instruments for performing the BKP treatment, the operator forms a path that reaches the spongin in the vertebral body through bone tissue based on the needle. The operator arranges a balloon that is inflatable in the vertebral body, on the spongin in the vertebral body, through the path. Thereby, the balloon is ready to be inflated.

FIG. 10 is a flowchart illustrating an example of an operation for the processing circuitry 1113 of the image-processing apparatus 111 illustrated in FIG. 1 guiding injection of a medium into the balloon. Once the balloon is ready to be inflated, the operator designates the vertebral body region targeted for treatment in the perspective image through the input interface 19.

Once the vertebral body region targeted for treatment is designated, the processing circuitry 1113 performs the display-control function 1113b. Once the display-control function 1113b is performed, the processing circuitry 1113 superimposes an image of a shape in a favorable condition of the vertebral body targeted for treatment onto a region in the perspective image where the vertebral body targeted for treatment is presented (step S101).

Specifically, the processing circuitry 1113 reads, from the memory 1111, data related to the shape in a favorable condition of the vertebral body targeted for treatment. If the data related to the shape in a favorable condition consists of three-dimensional information, a cross section that represents the shape needs to be specified. If the path for the insertion of a needle has been determined in the preoperative simulation, the processing circuitry 1113 determines, as the cross section that represents the shape, the cross section along A-A', designated when determining the insertion path. The processing circuitry 1113 obtains information on the cross section along A-A' among the pieces of shape-related information and generates a shape image.

If the path for the insertion of a needle has not been determined in the preoperative simulation, position adjustment is made, for example, between the medical image of the subject 150 obtained before surgery and the perspective image obtained during surgery. The position adjustment between the two images may be performed, for example, using an existing technique. Once the path for the insertion of a needle is determined, the processing circuitry 1113 specifies a cross section corresponding to the determined insertion path on the medical image based on the positional information of the holding device 16 and the bed unit 17. The processing circuitry 1113 obtains information on the cross section specified on the medical image among the pieces of shape-related information read from the memory 1111, and generates a shape image.

For example, if a perspective image is obtained from a different projection angle during surgery, the processing circuitry 1113 may generate a shape image in line with the obtained perspective image. Based on the positional information of the holding device 16 and the bed unit 17, for example, the processing circuitry 1113 specifies a cross section on the medical image that corresponds to the perspective image obtained from a different projection angle. The processing circuitry 1113 obtains information on the cross section specified on the medical image among the pieces of shape-related information read from the memory 1111, and generates a shape image.

If the data related to the shape in a favorable condition consists of two-dimensional information, the processing circuitry 1113 generates a shape image based on the shape-related information read from the memory 1111.

Next, the processing circuitry 1113 determines a position on the perspective image on which the shape image is superimposed. The position on which the shape image is superimposed is determined, for example, by designation of the position on the perspective image by the operator. Also, the position on which the shape image is superimposed is determined, for example, by associating a part of the shape image with a part of the perspective image through existing pattern-matching processing. The way of displaying the shape image can be determined discretionarily according to an instruction from the operator. For example, only a boundary of the vertebral body region may be displayed. Alternatively, the perspective image may be displayed visibly by decreasing the opacity, and the entire vertebral body region to be superimposed may be displayed visibly. The processing circuitry 1113 superimposes the shape image on the determined position on the perspective image. FIG. 11 is a schematic diagram illustrating an example of displaying the image of the shape of the vertebral body in a favorable condition, superimposed on the vertebral body targeted for treatment in the perspective image.

The shape image obtained in the preoperative simulation need not necessarily be superimposed onto the perspective image. The operator may draw the shape of the vertebral body in a favorable condition by himself, or herself, based on the shape of the vertebral body presented on the perspective image.

Also, the timing of the superimposition of the image of the shape of the vertebral body in a favorable condition onto the perspective image is not limited to a timing after the balloon is ready to be inflated. The shape image may be superimposed onto the perspective image when, for example, the positions of the holding device 16 and the bed unit 17 are determined. At this time, the opacity of the shape image may be set discretionarily through the input interface 19. For example, when inserting a needle into the vertebral body, the opacity of the shape image may be decreased, so that the shape image is invisible on the perspective image.

Once the shape image superimposed onto the perspective image is displayed, the operator starts injecting a medium such as a sterile fluid into the balloon. Once the medium is injected into the balloon, the balloon inflates in the vertebral body and compresses the spongin in the vertebral body. Due to the compression, an inner cavity is formed in the spongin.

Once the shape image superimposed onto the perspective image is displayed, the processing circuitry 1113 performs the determination function 1113c. By performing the determination function 1113c, the processing circuitry 1113 compares, in a preset cycle, a shape of the vertebral body presented in the perspective image with a shape superimposed onto the vertebral body in the perspective image, and determines whether the balloon has inflated sufficiently or not (step S102). Specifically, the processing circuitry 1113 extracts the vertebral body region presented in the perspective image by, for example, image-analysis processing. The processing circuitry 1113 calculates an area of the extracted vertebral body region in a preset cycle, for example, by using the number of pixels. Once the area of the extracted vertebral body region is calculated, the processing circuitry 1113 compares the calculated area with an area of the vertebral body region in a favorable condition that is superimposed, and determines whether or not these areas are closest to each other. For example, the processing circuitry 1113 subtracts the calculated area from the area of the vertebral body region in a favorable condition, and if the value obtained thereby is smaller than a preset area, the processing circuitry 1113 determines that the two areas are most proximate to each other. When the processing circuitry 1113 determines that the two areas are most proximate to each other, the processing circuitry 1113 determines that the balloon has inflated sufficiently.

When the processing circuitry 1113 determines that the balloon has inflated sufficiently, the processing circuitry 1113 performs the notification function 1113d. By performing the notification function 1113d, the processing circuitry 1113 notifies the operator of warnings that the balloon has inflated sufficiently, that the inflation of the balloon is to be stopped, etc. (step S103). For example, the processing circuitry 1113 displays notifications such as "The balloon has inflated sufficiently" and "Please stop inflating the balloon" on the display 15. If the X-ray diagnostic apparatus 10 includes a speaker, the above notifications may be given by sound through the speaker.

When the operator confirms the notifications displayed on the display 15, for example, the operator stops injecting the medium into the balloon. Then, the operator deflates the balloon by sucking the medium injected into the balloon, and pulls out the deflated balloon from the inside of the vertebral body. Once the operator pulls out the balloon, the operator injects bone cement into the cavity in the vertebral body formed by inflation of the balloon. When starting the injection the bone cement, for example, the operator inputs, from the input interface 19, initiation of injecting the bone cement. An injection device for injecting the bone cement may notify the X-ray diagnostic apparatus 10 that injection of the bone cement has been started.

FIG. 12 is a flowchart illustrating an example of an operation for the processing circuitry 1113 of the image-processing apparatus 111 (illustrated in FIG. 1), guiding injection of the bone cement into the vertebral body.

Once the initiation of injection of the bone cement is detected (step S121), the processing circuitry 1113 performs the determination function 1113c. By performing the determination function 1113c, the processing circuitry 1113 determines whether or not the bone cement has been injected sufficiently (step S122). Specifically, the processing circuitry 1113 reads, from the memory 1111, data related to the deformation amount estimated in the preoperative simulation. The rate at which the bone cement is injected from the injection device is known. Based on the rate of injection, the processing circuitry 1113 calculates the time required to inject, into the vertebral body, a volume of bone cement corresponding to the deformation amount read. The processing circuitry 1113 determines whether the calculated time has elapsed since the injection of the bone cement was started. If the calculated time has elapsed since the injection of the bone cement was started, the processing circuitry 1113 determines that the bone cement has been injected sufficiently. The processing circuitry 1113, by knowing the volume of the bone cement injected, may determine that the bone cement has been injected sufficiently when the volume of the bone cement injected reaches the read deformation amount.

When the processing circuitry 1113 determines that the bone cement has been injected sufficiently, the processing circuitry 1113 performs the notification function 1113d. By performing the notification function 1113d, the processing circuitry 1113 notifies the operator of warnings that the amount of the bone cement injected is close to the expected volume, that the injection of the bone cement is to be stopped, etc. (step S123). For example, the processing circuitry 1113 displays notifications such as "The amount of the bone cement injected is close to the expected volume" and "Please stop injecting the bone cement" on the display 15. If the X-ray diagnostic apparatus 10 includes a speaker, the above notifications may be given by sound through the speaker.

When the operator confirms the notifications displayed on the display 15, for example, the operator stops injecting the bone cement into the vertebral body. Then, the operator detaches the instruments attached to the subject 150, sutures and closes the incised part, and ends the BKP treatment.

As described above, the processing circuitry 1113 of the X-ray diagnostic apparatus 10 determines whether or not the amount of the bone cement injected into the vertebral body substantially matches the deformation amount estimated in the preoperative simulation. When the amount of the bone cement injected into the vertebral body substantially matches the deformation amount estimated in the preoperative simulation, the processing circuitry 1113 notifies the operator of a warning regarding injection of the bone cement. Thereby, the processing circuitry 1113 can prevent injection, into the vertebral body, of an amount of bone cement exceeding the amount of deformation of the vertebral body.

Also, the processing circuitry 1113 superimposes an image of the vertebral body in a normal condition onto the vertebral body region included in the perspective image. The processing circuitry 1113 determines whether or not the shape of the vertebral body in the perspective image substantially matches the superimposed shape of the vertebral body as a result of the inflation of the balloon. When the shape of the vertebral body in the perspective image substantially matches the shape of the vertebral body superimposed, the processing circuitry 1113 notifies the operator of a warning regarding inflation of the balloon. Thereby, the processing circuitry 1113 can prevent inflation of the balloon beyond the normal condition.

A favorable shape of the vertebral body targeted for treatment that is superimposed onto the perspective image by the processing circuitry 1113, and performing the display-control function 1113b, is not limited to the shape estimated in the preoperative simulation or the shape drawn by the operator. The processing circuitry 1113 may obtain the favorable shape by analyzing the perspective image in real time. Specifically, the processing circuitry 1113 performs an image analysis on the perspective image, and extracts the vertebral body regions of the vertebral bodies above and below the vertebral body targeted for treatment. The processing circuitry 1113 determines, as the vertebral body region in a favorable condition of the vertebral body targeted for treatment, a region obtained by averaging a distribution of the extracted vertebral body regions.

Other Embodiments

Figure 13:
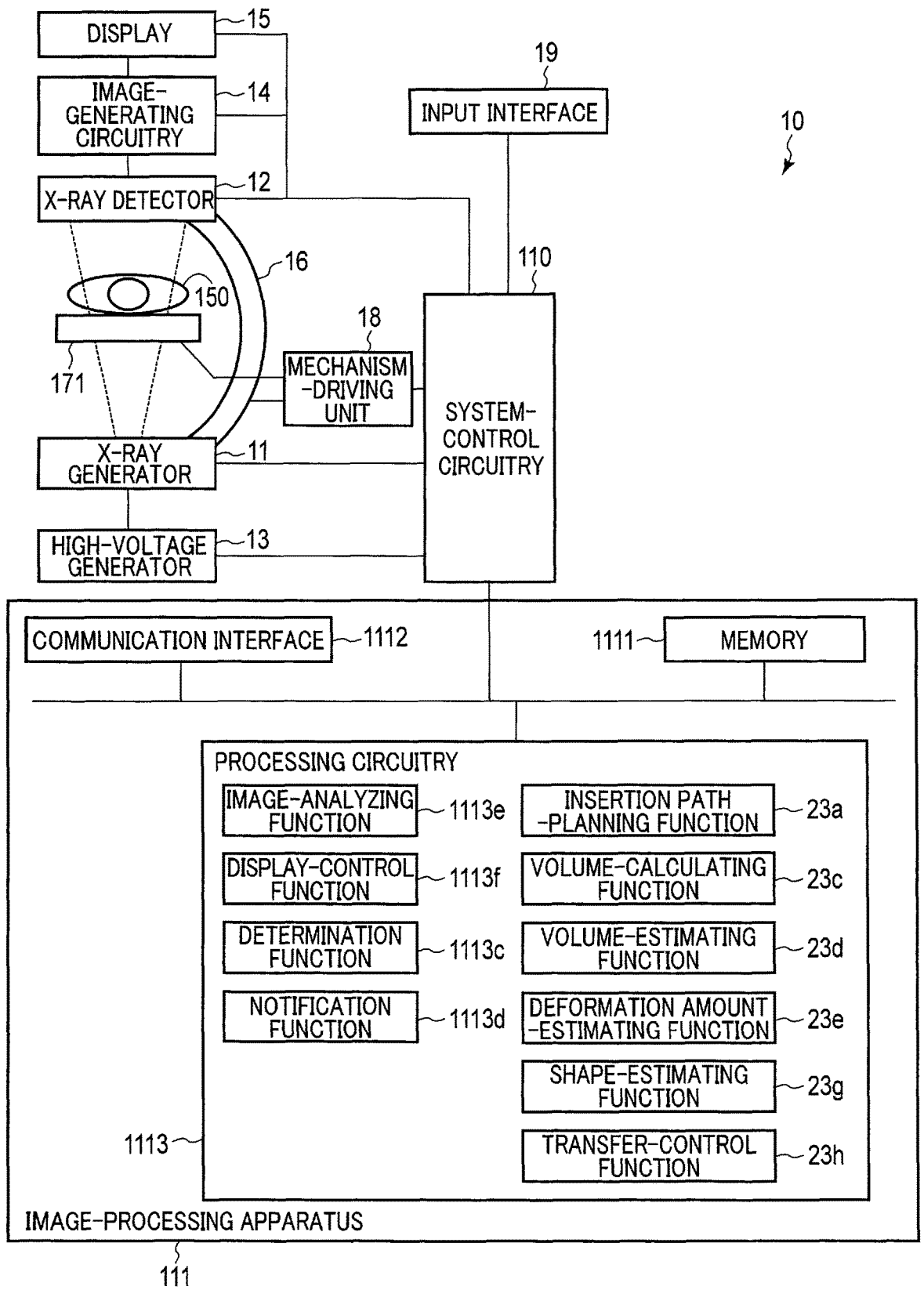
FIG. 13 is a diagram illustrating another embodiment of the support information-generation apparatus.

In the first embodiment, the case where the server apparatus 20 performs the preoperative simulation for the BKP treatment is described as an example. However, the configuration is not limited to this. For example, the X-ray diagnostic apparatus 10 may function to perform the preoperative simulation. FIG. 13 is a diagram illustrating an example of another embodiment of the support information-generation apparatus 1. The support information-generation apparatus 1 illustrated in FIG. 13 includes the X-ray diagnostic apparatus 10. The processing circuitry 1113 included in the image-processing apparatus 111 of the X-ray diagnostic apparatus 10 has an image-analyzing function 1113e, a display-control function 1113f, the determination function 1113c, the notification function 1113d, the insertion path-planning function 23a, the volume-calculating function 23c, the volume-estimating function 23d, the deformation amount-estimating function 23e, the shape-estimating function 23g, and the transfer-control function 23h.

In the first embodiment, the case where the X-ray diagnostic apparatus 10 notifies the operator of the BKP treatment that the inflation of the balloon is sufficient and that the amount of injection of the bone cement into the vertebral body is sufficient is described as an example. However, an apparatus that gives these notifications is not limited to the X-ray diagnostic apparatus 10. For example, a warning information-notification apparatus 40 may give such notifications.

Figure 14:
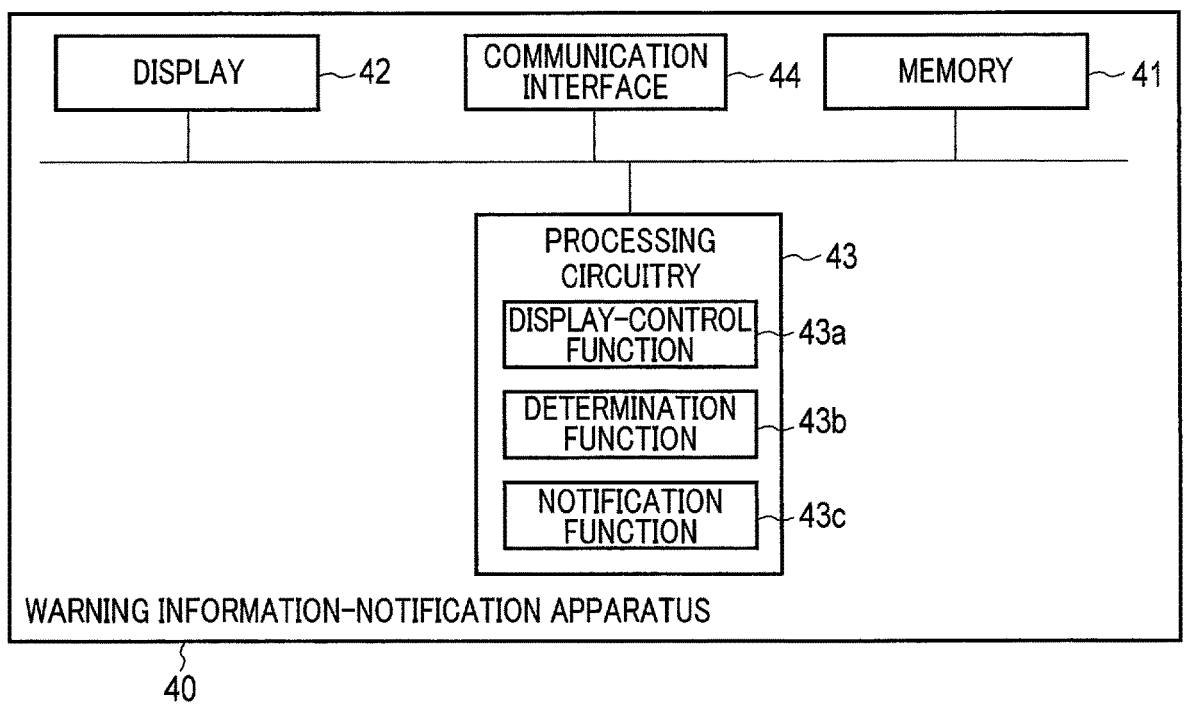
FIG. 14 is a block diagram illustrating a functional configuration of a warning information-notification apparatus according to the first embodiment.

FIG. 14 is a block diagram illustrating an example of a functional configuration of the warning information-notification apparatus 40 according to the first embodiment. The warning information-notification apparatus 40 illustrated in FIG. 14 includes a memory 41, a display 42, a communication interface 44, and processing circuitry 43.

The memory 41 includes, for example, a magnetic or optical storage medium, or a processor-readable storage medium such as a semiconductor memory. The memory 41 stores, for example, a warning information-generation program. The memory 41 stores, for example, perspective image data generated by the image-generating circuitry 14 of the X-ray diagnostic apparatus 10 and data generated by the server apparatus 20. The data generated by the server apparatus 20 includes, for example, the data related to the amount of deformation of the vertebral body targeted for the BKP treatment during the treatment. Also, the data generated by the server apparatus 20 may include, for example, the data related to the shape in a favorable condition of the vertebral body targeted for the BKP treatment.

The display 42 displays, for example, a perspective image based on the perspective image data and warning information according to instructions from the processing circuitry 43.

The processing circuitry 43 is, for example, a processor functioning as a main unit of the warning information-notification apparatus 40. The processing circuitry 43 executes a control program stored in the memory 41 to thereby accomplish functions corresponding to the program. The processing circuitry 43 has, for example, a display-control function 43a, a determination function 43b, and a notification function 43c. In the present embodiment, a case where the display-control function 43a, the determination function 43b, and the notification function 43c are fulfilled by a single processor is described; however, the present embodiment is not limited thereto.

The display-control function 43a is a function to control display of perspective image data by the display 42. Specifically, with the display-control function 43a, for example, the processing circuitry 43 displays, on the display 42, a perspective image based on the perspective image data generated by the image-generating circuitry 14. The processing circuitry 43 superimposes a favorable shape of the vertebral body targeted for treatment onto the perspective image.

The determination function 43b is a function to determine whether or not an inflation of a balloon is sufficient, and whether or not an amount of injection of bone cement into the vertebral body is sufficient. Specifically, with the determination function 43b, for example, the processing circuitry 43 compares a shape of the vertebral body presented in the perspective image with a favorable shape superimposed onto the vertebral body in the perspective image. If the actual shape of the vertebral body substantially matches the favorable shape, the processing circuitry 43 determines that the balloon has inflated sufficiently.

The processing circuitry 43 determines whether or not an amount of bone cement injected into the vertebral body matches an amount of bone cement calculated in the preoperative simulation performed by the server apparatus 20. If the amount of bone cement injected matches the amount of bone cement calculated, the processing circuitry 43 determines that bone cement has been injected sufficiently.

The notification function 43c is a function to notify that the inflation of the balloon is sufficient and that the amount of injection of bone cement into the vertebral body is sufficient. Specifically, with the notification function 43c, for example, the processing circuitry 43 notifies the operator that the inflation of the balloon is sufficient when the inflation of the balloon is sufficient. Also, when the amount of injection of bone cement into the vertebral body is sufficient, the processing circuitry 43 notifies the operator that the amount of injection of bone cement into the vertebral body is sufficient. The notification to the operator may be made by sound or displayed by the display 42.

Once the BKP treatment is started, the warning information-notification apparatus 40 is, for example, connected to the X-ray diagnostic apparatus 10 via the communication interface 44, so that the warning information-notification apparatus 40 is prepared for the inflation of the balloon and injection of the bone cement into the vertebral body.

The warning information-notification apparatus 40 may give only a notification that the amount of the bone cement injected into the vertebral body is sufficient. In this case, the memory 41 need not store, for example, the perspective image data generated by the image-generating circuitry 14 of the X-ray diagnostic apparatus 10. The processing circuitry 43, with the determination function 43b, determines only whether or not the amount of injection of the bone cement into the vertebral body is sufficient, and with the notification function 43c, notifies the operator that the amount of injection of the bone cement into the vertebral body is sufficient.

In the first embodiment, the case where the support information-generation apparatus 1 includes the X-ray diagnostic apparatus 10 is described as an example. However, a medical diagnostic imaging apparatus used in the support information-generation apparatus 1 is not limited to the X-ray diagnostic apparatus 10. An X-ray CT apparatus may be employed instead of the X-ray diagnostic apparatus 10 as long as imaging can be performed in real time.

According to at least one embodiment described above, the support information-generation apparatus can reduce the risk of rupture of the balloon during surgery, and/or the risk of leakage of the bone cement to the exterior of the vertebral body during surgery.

The term "processor" used in the above descriptions of the embodiments means, for example, circuitry such as a central processing unit (CPU), a graphics processing unit (GPU), an application specific integrated circuit (ASIC), and a programmable logic device (e.g., a simple programmable logic device (SPLD), a complex programmable logic device (CPLD), a field programmable gate array (FPGA)). The processor implements functions by reading and executing a program stored in the storage circuitry. Instead of storing a program in the storage circuitry, the program may be directly incorporated into the circuitry of the processor. In this case, the processor implements functions by reading and executing the program incorporated into the circuitry. Each processor of the above-described embodiments is not limited to being configured as single circuitry, but may include a plurality of units of independent circuitry to implement the functions of the processor. Furthermore, a plurality of constituent elements described in the above embodiments may be integrated into one processor to implement the functions thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A support information-generation apparatus comprising processing circuitry configured to:
    extract a vertebral body region from a medical image obtained before surgery and calculate a first volume of a vertebral body targeted for treatment by percutaneous vertebroplasty based on the extracted vertebral body region;
    estimate a second volume of the targeted vertebral body related to an estimated shape after the treatment; and
    calculate, based on a difference between the first volume and the second volume, a volume of an object to be inserted so as to deform the targeted vertebral body into the estimated shape.

2. The support information-generation apparatus according to claim 1, wherein the processing circuitry is configured to present the calculated volume as an amount of inflation of a balloon and/or an amount of injection of bone cement.

3. The support information-generation apparatus according to claim 1, further comprising:
    an X-ray generator;
    an X-ray detector configured to detect X-rays radiated from the X-ray generator; and
    image-generating circuitry configured to generate a perspective image based on the detected X-rays,
    wherein the processing circuitry is configured to:
        determine whether or not an amount of bone cement injected into the vertebral body substantially matches the calculated volume; and
        provide notification of a warning regarding injection of the bone cement if the amount of the bone cement injected into the vertebral body substantially matches the calculated volume.

4. The support information-generation apparatus according to claim 3, wherein the processing circuitry is configured to:
    perform estimation based on the vertebral body region extracted from the medical image, to obtain the estimated shape;
    display the perspective image in such a manner that a shape image of the estimated shape is superimposed on a vertebral body region included in the perspective image;
    determine whether or not a shape of a vertebral body included in the perspective image substantially matches the superimposed shape image by inflation of a balloon; and
    provide notification of a warning regarding inflation of the balloon if the shape of the vertebral body included in the perspective image substantially matches the superimposed shape image.

5. The support information-generation apparatus according to claim 4, wherein the processing circuitry is configured to determine a cross section based on a projection angle, and determine a shape of the estimated shape on the cross section as the shape image.

6. The support information-generation apparatus according to claim 4, wherein the processing circuitry is configured to:
 determine a path for insertion of a needle into a vertebral body based on designation input with respect to the vertebral body region included in the medical image; and
 display the perspective image in such a manner that a shape image of the estimated shape with respect to a plane that includes the determined insertion path is superimposed on the vertebral body region included in the perspective image.

7. The support information-generation apparatus according to claim 1, wherein the processing circuitry is configured to determine a path for insertion of a needle into a vertebral body based on designation input with respect to the vertebral body region included in the medical image.

8. The support information-generation apparatus according to claim 7, wherein the processing circuitry is configured to select a balloon having a size suited to the targeted vertebral body based on the determined insertion path.

9. A support information-generation apparatus comprising:
 an X-ray generator;
 an X-ray detector configured to detect X-rays radiated from the X-ray generator;
 image-generating circuitry configured to generate a perspective image based on the detected X-rays; and
 processing circuitry configured to:
  determine whether or not an amount of bone cement injected into a vertebral body targeted for treatment by percutaneous vertebroplasty substantially matches an amount of deformation of the vertebral body in the treatment, the amount of deformation of the vertebral body in the treatment estimated based on a medical image obtained before surgery; and
  provide notification of a warning regarding injection of the bone cement if the amount of the bone cement injected into the vertebral body substantially matches the estimated amount of deformation of the vertebral body.

10. The support information-generation apparatus according to claim 9, wherein the processing circuitry is configured to:
 display the perspective image in such a manner that a shape image of an estimated shape of the targeted vertebral body after the treatment is superimposed on a vertebral body region included in the perspective image, wherein the estimated shape is obtained based on a vertebral body region extracted from the medical image;
 determine whether or not a shape of a vertebral body included in the perspective image substantially matches the superimposed shape image by inflation of a balloon; and
 provide notification of a warning regarding inflation of the balloon if the shape of the vertebral body included in the perspective image substantially matches the superimposed shape image.

11. The support information-generation apparatus according to claim 10, wherein the processing circuitry is configured to display the perspective image in such a manner that a shape image of the estimated shape, with respect to a plane that includes a determined insertion path, is superimposed on the vertebral body region included in the perspective image.

12. A support information-generation method, comprising:
 extracting a vertebral body region from a medical image obtained before surgery;
 calculating a first volume of a vertebral body targeted for treatment by percutaneous vertebroplasty based on the extracted vertebral body region;
 estimating a second volume of the targeted vertebral body related to an estimated shape after the treatment;
 calculating, based on a difference between the first volume and the second volume, a volume of an object to be inserted so as to deform the targeted vertebral body into the estimated shape;
 determining whether or not an amount of bone cement injected into the vertebral body substantially matches the calculated volume; and
 providing notification of a warning regarding injection of the bone cement if the amount of the bone cement injected into the vertebral body substantially matches the calculated volume.

13. A warning information-notification apparatus, comprising processing circuitry configured to:
 determine whether or not an amount of bone cement injected into a vertebral body targeted for treatment by percutaneous vertebroplasty substantially matches an amount of deformation of the vertebral body in the treatment, the amount of deformation of the vertebral body in the treatment estimated based on a medical image obtained before surgery; and
 provide notification of a warning regarding injection of the bone cement if the amount of the bone cement injected into the vertebral body substantially matches the estimated amount of deformation of the vertebral body in the treatment.

* * * * *